United States Patent [19]
Martineau et al.

[11] Patent Number: 5,530,185
[45] Date of Patent: Jun. 25, 1996

[54] USE OF OVARY-TISSUE TRANSCRIPTIONAL FACTORS

[75] Inventors: Belinda M. Martineau; David M. Stalker, both of Davis, Calif.; Ann A. Reilley, Fort Collins, Colo.

[73] Assignee: Calgene, Inc., Sacramento, Calif.

[21] Appl. No.: 998,158

[22] Filed: Dec. 29, 1992

Related U.S. Application Data

[63] Continuation-in-part of Ser. No. 554,195, Jul. 17, 1990, Pat. No. 5,175,095, which is a continuation-in-part of Ser. No. 382,518, Jul. 19, 1989, abandoned.

[51] Int. Cl.$^6$ .............................. A01H 5/00; C12N 15/82; C12N 15/00
[52] U.S. Cl. .................. 800/205; 800/250; 800/DIG. 27; 435/172.3; 435/240.4; 435/320.1; 536/23.1; 536/23.2; 536/23.7; 536/24.1; 935/35; 935/60; 935/64
[58] Field of Search ................................. 435/69.1, 172.3, 435/370, 240.4; 800/205, 255, DIG. 27, 250; 935/6, 35, 67; 536/23.1, 23.2, 23.4, 23.7, 24.1

[56] References Cited

U.S. PATENT DOCUMENTS

| | | | |
|---|---|---|---|
| 4,801,540 | 1/1989 | Hiatt | 435/172.3 |
| 4,943,674 | 7/1990 | Houck | 800/205 |
| 5,004,863 | 4/1991 | Umbeck | 800/205 |
| 5,159,135 | 10/1992 | Umbeck | 800/205 |

FOREIGN PATENT DOCUMENTS

| | | |
|---|---|---|
| 0255378A2 | 2/1988 | European Pat. Off. . |
| 88/09334 | 12/1988 | WIPO . |
| 89/12386 | 12/1989 | WIPO . |
| WO92/15675 | 9/1992 | WIPO . |

OTHER PUBLICATIONS

E Firoozabady et al (1987) Plant Mol Biol 10:105–116.
V Bernan et al (1985) Gene 37:101–110.
C S Gasser et al (1989) Plant Cell 1:15–24.
G Della–Cioppa et al. (1987) Plant Physiol 84:965–968.
M Bevan (1984) Nucleic Acids Research 12:8711–8721.
A R vanderKrol et al (1988) Nature 333:866–869.
Graham, et al., *Journal of Biological Chemistry* (Jun. 10, 1985) vol. 260, No. 11:6561–6564.
John and Crow, *Proc. Natl. Acad. Sci. (USA)* (Jul. 1992) vol. 89:5769–5773.
Kridl, et al., *Seed Science Research* (1991) vol. 1:209–219.
Radke, et al., *Theor. Appl. Genet.* (1988) vol. 75:685–694.
Radke, et al., *Plant Cell Reports* (1992) vol. 11:499–505.
Murai, et al., (1993) *Science* 222:476–482.
Larkins, et al., (1985) *J. Cell Biochem.* Suppl. 9C:264.
Barker, et al., (1983) *Plant Mol. Biol.* 2:335–350.
McCormick, et al., (1987) *Tomato Biotechnol.*, Nevins et al., eds., Alan R. Liss, Inc.: New York, pp. 255–265.
Piechulla, et al., (1986) *Plant Mol. Biol.* 7:367–376.
Grierson, et al., (1986) *Nucleic Acids Res.* 14:8585–8603.
McCormick, et al., (1986) *Plant Cell. Rep.* 5:81–84.
Bird, C. R. et al., "The tomato polygalaturonase gene and ripening–specific expression in transgenic plants" *Plant Molecular Biology* 11:651–662 (1988).

(List continued on next page.)

*Primary Examiner*—David T. Fox
*Assistant Examiner*—Bruce Campell
*Attorney, Agent, or Firm*—Barbara Rae-Venter; James A. Bradburne

[57] ABSTRACT

Novel DNA constructs are provided which may be used as molecular probes or inserted into a plant host to provide for modification of transcription of a DNA sequence of interest in ovary tissue, particularly in very early fruit development. The DNA constructs comprise a transcriptional initiation regulatory region associated with gene expression in ovary tissue from immediately prior to anthesis through flower senescence.

18 Claims, 11 Drawing Sheets

GENOMIC CLONE 116.

1 kb

OTHER PUBLICATIONS

Hiatt, W. R. et al., "Expresion of selected genes during tomato fruit maturation and ripening" *J. Cell Biochem* Supp. 0:148 (1988).

Benfey, P. N. and Chua, N., "Regulated Genes in Transgenic Plants" *Science* 244:174–181 (1989).

Martineau, B. and Houck, C. M., "Wound–Inducible Expression of a Gene From Tomato" *J. of Cellular Biochemistry* 14E:306 (1990).

Hass, G. M. and Hermodson, M. A., "Amino Acid Sequence of a Carboxypeptidase Inhibitor from Tomato Fruit" *Biochemistry* 20:2256–2260 (1981).

Gasser, C. S. et al., "Analysis of Floral Specific Genes," *J. Cellular Biochem* 12C:137 (1988).

Goldberg, R. B., "Plants: Novel Development Processes" *Science* 240:1460–1467 (1988).

1    AAAAAACAAAAAACATTTCTAATCTTTTTCACTCATTCCATGGCTCGTCGTTCCATTTTCTTCATGGCATTT                69

TTTTTTGTTTTTGTAAAGATTAGAAAAAGTGAGTAAGGTACCGAGCAAGGTAAAAGAAGTACCGTAAA
LysLysThrPheLeuIlePhePheThrHisSerMETAlaArgSerIlePhePheMETAlaPhe

70   TTGGTCTCTTGGCAATGATGCTCTTTGTTACCTATGAGGTAGAAGCTCAGCAAATTTGCAAAGCACCAAGC                138

AACCAGAACCGTTACTACGAGAGAAACAATGATACTCCATCTCCGAGTCGTTAAACGTTCGTTCGTTCG
LeuValLeuAlaMETMETLeuPheVALThrTyrGluValGluAlaGlnGlnIleCysLysAlaProSer

139  CAAACTTTCCCAGGATTATGTTTTATGGACTCATCATGTAGAAAATATTGTATCAAAGAGAAATTTACT                207

GTTTGAAAGGGTCCTAATACAAAATACCTGAGTAGTACATCTTTTATAACATAGTTTCTCTTTAAATGA
GlnThrPheProGlyLeuCysPheMETAspSerSerCysArgLysTyrCysIleLysGluLysPheThr

208  GGTGGACATTGTAGCAAACTCCAAAGGAAGTGTCTATGCACTAAGCCATGTGTATTTGACAAATCTCA                276

CCACCTGTAACATCGTTTGAGGTTTCCTTCACAGATACGTGATTCGGTACACATAAACTGTTTAGAGT
GlyGlyHisCysSerLysLeuGlnArgLysCysLeuCysThrLysProCysValPheAspLysIleSer

277  AGTGAAGTTAAAGCAACTTTGGGTGAGGAAGCAAAAACTCTAAGTGAAGTTGTGCTTGAAGAAGAGATT                345

TCACTTCAATTTCGTTGAAACCCACTCCTTCGTTTTGAGATTCACTTCAACACGAACTTCTTCTCTAA
SerGluValLysAlaThrLeuGlyGluAlaLysThrLeuSerGluValValLeuGluGluGluIle

346  ATGATGGAGTAATAATTAAGTGAGGTAAATAAGGATTTGAGTGTCAAAAAAACAAAATTAATAAAG                414

TACTACCTCATTATTAATTCACTCCATTTATTCCTAAAACTCACAGTTTTTTTGTTTAATTATTC
METMETGlu  .    .   LeuSerGluValLys  .  GlyPhe  .  ValSerLysLysThrLysLeuIleLys

FIGURE 1A

415 TGTTGCCTTTCTTATTAGGGTAGCTTGTGATGTTGTGTAGTATTGGCCTATAGTAGCCATTTGACAC
    ACAACGGAAAAGAATAATCCCATCGAACACTACAACACAATCATAACCGGATATCATCGGTAAACTGTG                    483
    CysCysLeuPheLeuLeuGly . LeuValMETLeuCys . TyrTrpProIleValAlaIle . His

484 ATTAAATAAGTTGTGACACATCATTAATCCTTATGTATGTTTAATGAAAAATGATCGACTACG
    TAATTTATTCAAACACTGTGTAGTAATTAGGAATACATACATACAAAATTACTTTTACTAGCTGATGC                      552
    IleLys . ValCysAspThrSerLeuIleLeuMETTyrValCysPheAsnGluLys . SerThrThr

553 ATCTTTAATTTT    564
    TAGAAATTAAAA
    IlePheAsnPhe

FIGURE 1B

```
   1  GCTCCACTACTCTCATCACTTAGTTCATCAAGCCTTCTTTATACCAA           49
  50  GGCATCAATCAATCTCATTAACAAAGTAGATTAGGGTTTTTCAAGATTTA         98
  99  GGATTCAATAGCTTCATCATGCTTATTTATCACAATTATATAATCACA          147
 148  TTCATACAAGCATACAATTCGCTATTAAGCATATAGAGCATAAGGGTTTACAATACTACCC  196
 197  AATACATATCATTCGCTATTAAGAGTTTACTACGAATAGCATAAACCAT         245
 246  AACCTACCTCCACCGAAGAATCGGATCAAACAATCTACTTTCCCAAAG          294
 295  CTGCGTTCTTCGTTTCTCTCTTGATCGTCGTTCTCCCTC                   343
 344  TCTTTGTTCTTCTATTTTTCTCAAACCCTCTCTTTCTTTTACCCTA            392
 393  ATTAGTATATAATTAAGTATAAAAGATGATAAAATACCCCATCTATTTG         441
 442  TTTGAAGGTTATCTCTTTTAGCCCCCAAGTAATTGAATTATTAACATTA         490
 491  AACCACTAACTTTATAATTATAAGCAGAATAGTCCAAAACGCCCCTTA          540
 540  AAATATTTAACAGAAATCCGACCCAGTCCTCCTGCATGCCCGTCACGCAGCCTGTANCG  588
 589  GNNCACAACTGTGACGGTCCGTCCGTCATGGCCGTCACAAAGTTCAGAG         637
 638  AGTTAATTTCTGTGGAAGATGTGTANGGTNGTCGTGCCACGACGGTCC          686
 687  GTCCTGTCATTTCGTTACGAAGTTCAGAGAGTCGATTTCAGTACCCAAA         735
         EcoRI

736  TTTCAGAATTCTAAGTGTTTTGGAACGAGACCCCNCGGTCCGTCGTGCC         784
               BamHI  SalI

785  CATGACGGTTCGTCGTGGGATCCGTCGACTCAGCCAGTTTTCCAAAAT          833
 834  TAAAATCTGCTGCTCAAAACGACTAAACAGTCGTTACAAAGTACTCAA          882
 883  TCAAATAAAAGAATAAATTCTTTTCCAAATACATATATTGTTTATAGG          931
 932  ACAGTGTTAACAGGGAAATGTAATCGTTGCCTCAATCGATTTTTTTTT          980
                   BglII

981  TGAAATTAAGATTGATTAGATCTTCTTTAAGATAACAATGTCTCAAAGA        1029
1030  TAAATTGAATGAATGAATTAGCTATATTCATTGAAAAGAAATTACT           1078
1079  AAAACAGATTGATAATAAAATAATAATAAATGACTTTGCATCTCTAAAATA      1127
```

*FIGURE 2A*

```
1128  GCTAGAAAGCAGATTTTTAAATAAAATACATATGATAAAAAAGATA      1176
1177  AATTAGAGTCATCCCATAAATAAATTCGCTTTAAATGTTGTTAAG       1225
1226  TCGGCCCTGAAAATAGGAATGGTATTAAATATTTTGTTTGATTTCACA    1274
1275  CTTGATATTTGACATTCATATTAATGGTAAAATATTTCCACACAAAACTATT 1323
1324  AGAGTGGTCTCACATTAATGCTAGAATCTGAAATATCTAATGTACTCCACCCAATTAA 1372
1373  TACAATCATAGCTAGAATCTGAAATATCTAATAAAAATATGTCTATTGCCAAA 1421
1422  TTAAAGATGATTTTTTGCTTAAATAAAAAAAATAAAATCAAGTGTA      1470
1471  CTACTAATAGATGTACTCACAAAAAAATTTGAAAATTTCATAAATGACCG  1519
1520  TATACAATGATTCGGAAGGCCATTTGTTTTCAGCATTTGTTTGTTTGTGA  1568
1569  TTTTACCCGTTCACAATTGTGTTTCAGCATTTGTTTTGGTTTGTGGA     1617
                                                HindIII
1618  TTTGGTTATGGAAGTTCAATAAAAAGTTGTGGTTTTATAAGCTTTGGAG   1666
1667  TTTTGAAAGGTTAAGTTGATTAAAAGTAGTGTTAGTGTCAATTGGAG     1715
1716  TTTCGTGTCTTGAAATAAATTTTATCACTTGCATTAGTTTCAAAATGTC   1764
1765  GAGTTGGTTAAGTAGAGTTTTTTCATTCGGAGTTTTTTATGAATT       1813
1814  TAAAATGTTAAGCTTAAGTTTATGAGAATTTTGAACCTTTGAGTTAATTT  1862
1863  TGATGCTTGAATTAAATTTTTGAGAATTTTTTGAAATCTGGGATAAT     1911
1912  GTTAGGTCTTAGAGAAGTCTGGTTGAATTTCATAGCTCAAGAGATTAG    1960
1961  TTTTGACTTTTTAGGCATTTGTTGGTTTATTACGATTTTCACGGACTT    2009
2010  TCGAATTAAGGAGACTTCGTGTCTTTATAAGGATTATACTTAAAAATAAA  2058
2059  TAGTTTTAAAAATCGTGTCTTTATAAGGATTATACTTAAAAATAAA      2107
2108  ATAAAATAAAGTACTACTAACATGTAATTCTGTCATAAGATAAGGTTGT   2156
2157  ACATTTAGGACTATTTGAATATTCATCAAAATAAAAAAAGTAGAGAT     2205

2206  GATAGTAATATAAATATTTATTTTTGATTTACATTTGATATTTTAATA    2254
2255  CTAACAATATGACATAATAAATTTGTATTCAGATTGTAAAATATTCCC    2303
2304  TAAAAAAAGATACTTTTACTGTGGCTCAAATTCAAATTTTCTAAG       2352
```

*FIGURE 2B*

| | | |
|---|---|---|
| 2353 | AAAAACTACTAATAATTGATTTCTAATTAAAATTTCGATATATATAT | 2401 |
| 2402 | ATATATATATATATATCATAATATACTTCACCTACCTCAATTATTATTA | 2450 |
| 2451 | TTTTCTTTTTTTTTACTTCACATATTTTTGGSCSACCAATTTTTTTT | 2499 |
| 2500 | TAACTTTTTGGTCTTACTCTTATTTCACTCCCTATAAATAACTCCCAT | 2548 |
| 2549 | TGTGTGATATTTTTATTCACAACTCTAACTTACACAATCTTTCTTATTATT | 2597 |

NcoI

| | | |
|---|---|---|
| 2598 | AAAAAAACAAAAACATTTCTAATCTTTTTCACTCATTCCATGGCTCGT | 2646 |
| 2647 | TCCATTTCTTCATGGCATTTTTGGTCTTGGCAATGATGCTCTTTGTTA | 2695 |
| 2696 | CCTATGgtttgtcttcataattattcctctaaaatcatcgcaataaaa | 2744 |
| 2745 | aaaaatgtaacgaagcagacatcagtaaaccgtttaaataaaccctaa | 2793 |
| 2794 | aaaaattgtgaattgatattacttgctatacgttaacaactatgataa | 2842 |
| 2843 | aaaaccctaaaaatatactttattcgatttcgtctctctcatgttattc | 2891 |
| 2892 | taactatttttgtgtgtgaatgattgtgaAGGTAGAAGCTCAGCAAAT | 2940 |
| 2941 | TTGCAAAGCACCAAGCCAAACTTTCCAGGATTATGTTTATGGACTCA | 2989 |
| 2990 | TCATGTAGAAAATATTGTATCAAAGAGAAATTTACTGGTGGACATTGTA | 3038 |
| 3039 | GCAAACTCCAAAGGAAGTGCTATGCACTAAGCCATGTGTATTTGACAA | 3087 |
| 3088 | AATCTCAAGTGAAGTTAAAGCAACTTGGGTGAGGAAGCAAAAACTCTA | 3136 |
| 3137 | AGTGAAGTTGTGCTTGAAGAAGAGATTATGATGGAGTAATAATTAAGTG | 3185 |
| 3186 | AGGTTAAAATAAGGATTTTGAGTGTCAAAAAAACAAAATTAATAAAGTG | 3234 |
| 3235 | TTGCCTTTTCTTATTAGGGTAGCTTGTGATGTTGTGACACATCATTAATCC | 3283 |
| 3284 | ATAGTAGCCATTTGACACATTAAATAAGTTTGTGACACTACGATCATTAATCC | 3332 |
| 3333 | TTATGTATGTTTTAATTAATGAAAAATGATCGACTACGATCTTTAATT | 3381 |
| 3382 | TATGTTTTACATTTAATCACTTTCTGTTACGATTCATTTATCTAG | 3430 |
| 3431 | TTATGAATGAAATATAGAGTGATTGAAGTAAGGAGCTAGTCTTCAAAC | 3479 |
| 3480 | AAAGACGTACATATGTACAAAGTAGGGTACTATTAAACTTCTTTTTAT | 3528 |

FIGURE 2C pZ70

1   ATTATTATTACCATGGCACAAAAATTTACTATCCTTTCACCATTCTCCTTGTGGTTATTGCTGCTCAA   69
          METAlaGlnLysPheThrIleLeuPheThrIleLeuLeuValValIleAlaAlaGln
                              Mature Protein Start

70  GATGTGATGGCACAAGATGCAACTCTGACGAAACTTTTCAGCAATATGATCCAGTTTGTCACAAACCT   138
    AspValMETAlaGlnAspAlaThrLeuThrLysLeuPheGlnGlnTyrAspProValCysHisLysPro

139 TGCTCAACACAAGACGATTGTTCTGGTGTACGTTCTCGTCAGGCCTGTTGGAGGTTCGCGGGGACATGT   207
    CysSerThrGlnAspAspCysSerGlyValArgPheCysGlnAlaCysTrpArgPheAlaGlyThrCys
    Mature Protein End

208 GGGCCCTATGTTGGGCGCGCCATGGCCATAGGCCGTGATTACAATTTCGTTGTTCTTCTTTTTCGACT   276
    GlyProTyrValGlyArgAlaMETAlaIleGlyVal

277 TTTTAATCCCAAGTGAATAAAGTCTAATTCGAAAAAGAAGAAAAAGTATCTATGTCTGAGTTATATGT   345

346 TTTGTGGCTAATAAGAAATCGACTATGCTTGTTGATTTGATAAAAATTATGTCATTAGGGTGTGATATG   414

415 TAATCATCAAATTAAAATAAAAATCATCGCATTGTGTGTG   453

FIGURE 4

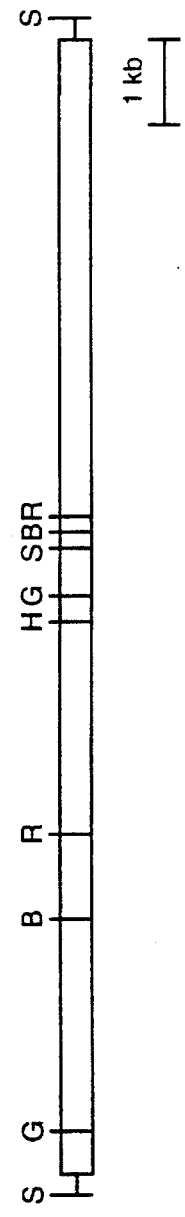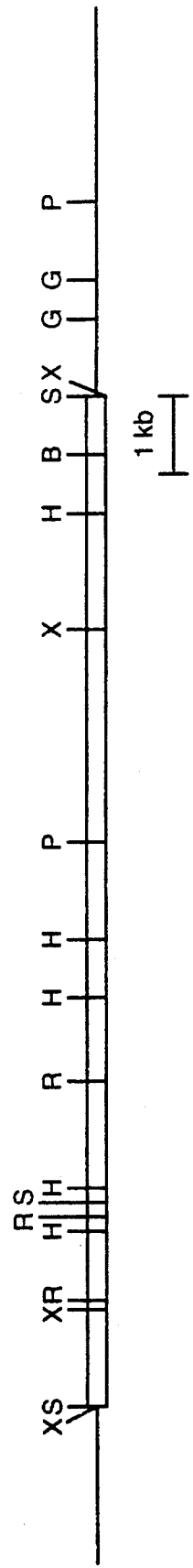
FIGURE 3
FIGURE 5

5,530,185

USE OF OVARY-TISSUE TRANSCRIPTIONAL FACTORS

CROSS-REFERENCE TO RELATED APPLICATIONS

This application is a continuation in part of U.S. application Ser. No. 554,195 filed Jul. 17, 1990, U.S. Pat. No. 5,175,095, which is a continuation-in-part of U.S. application Ser. No. 382,518, abandoned, filed Jul. 19, 1989, which applications are incorporated herein by reference.

INTRODUCTION

Technical Field

This invention relates to methods of using in vitro constructed DNA transcription or expression cassettes capable of directing ovary-tissue transcription of a DNA sequence of interest in plants to produce ovary-derived cells having an altered phenotype. The invention is exemplified by methods of using ovary tissue promoters for altering the phenotype of cotton fibers, and cotton fibers produced by the method.

Background

In general, genetic engineering techniques have been directed to modifying the phenotype of individual prokaryotic and eukaryotic cells, especially in culture. Plant cells have proven more intransigent than other eukaryotic cells, due not only to a lack of suitable vector systems but also as a result of the different goals involved. For many applications, it is desirable to be able to control gene expression at a particular stage in the growth of a plant or in a particular plant part. For this purpose, regulatory sequences are required which afford the desired initiation of transcription in the appropriate cell types and/or at the appropriate time in the planes development without having serious detrimental effects on plant development and productivity. It is therefore of interest to be able to isolate sequences which can be used to provide the desired regulation of transcription in a plant cell during the growing cycle of the host plant.

One aspect of this interest is the ability to change the phenotype of particular cell types, such as differentiated epidermal cells that originated in ovary tissue, so as to provide for altered or improved aspects of the mature cell type. In order to effect the desired phenotypic changes, transcription initiation regions capable of initiating transcription only in early ovary development are used. These transcription initiation regions are active prior to the onset of pollination and are less active or inactive, before fruit enlargement, tissue maturation, or the like occur.

Relevant Literature

A class of fruit-specific promoters expressed at or during anthesis through fruit development, at least until the beginning of ripening, is discussed in European Application 88.906296.4, the disclosure of which is hereby incorporated by reference. cDNA clones that are preferentially expressed in cotton fiber have been isolated. One of the clones isolated corresponds to mRNA and protein that are highest during the late primary cell wall and early secondary cell wall synthesis stages. John Crow PNAS (1992) 89:5769–5773. cDNA clones from tomato displaying differential expression during fruit development have been isolated and characterized (Mansson et al., *Mol. Gen. Genet.* (1985) 200:356–361: Slater et al., *Plant Mol. Biol.* (1985) 5:137–147). These studies have focused primarily on mRNAs which accumulate during fruit ripening. One of the proteins encoded-by the ripening-specific cDNAs has been identified as polygalacturonase (Slater et al., *Plant Mol. Biol.* (1985) 5:137–147). A cDNA clone which encodes tomato polygalacturonase has been sequenced (Crierson et al., *Nucleic Acids Research* (1986) 14:8395–8603). Improvements in aspects of tomato fruit storage and handling through transcriptional manipulation of expression of the polygalacturonase gene have been reported (Sheehy et al., *Proc. Natl. Acad. Sci.* USA (1988) 85:8805–8809; Smith et at., *Nature* (1988) 334: 724–726).

Mature plastid mRNA for psbA (one of the components of photosystem II) reaches its highest level late in fruit development, whereas after the onset of ripening, plastid mRNAs for other components of photosystem I and II decline to nondetectable levels in chromoplasts (Piechulla et al., *Plant Molec. Biol.* (1986) 7:367–376). Recently, cDNA clones representing genes apparently involved in tomato pollen (McCormick et al., *Tomto Biotechnology* (1987) Alan R. Liss, Inc., N.Y.) and pistil (Gasser et al., *Plant Cell* (1989), 1:15–24) interactions have also been isolated and characterized.

Other studies have focused on genes inducibly regulated, e.g. genes encoding sefine proteinase inhibitors, which are expressed in response to wounding in tomato (Graham et al., *J. Biol. Chem.* (1985) 260:6555–6560: Graham et al., *J. Biol. Chem.* (1985) 260:6561–6554) and on mRNAs correlated with ethylene synthesis in ripening fruit and leaves after wounding (Smith et al., *Planta* (1986) 168: 94–100). Accumulation of a metallocarboxypeptidase inhibitor protein has been reported in leaves of wounded potato plants (Graham et al., *Biochem BioPhysRes Comm.* (1981) 101:1164–1170).

Genes which are expressed preferentially in plant seed tissues, such as in embryos or seed coats, have also been reported. See, for example, European Patent Application 87306739.1 (published as 0 255 378 on Feb. 3, 1988) and Kridl et al. (Seed Science Research (1991) 1:209–219).

Agrobacterium-mediated cotton transformation is described in Umbeck, U.S. Pat. Nos. 5,004,863 and 5,159, 135 and cotton transformation by particle bombardment is reported in WO 92/15675, published Sep. 17, 1992. Transformation of Brassica has been described by Radke et al. (Theor. Appl. Genet. (1988) 75;685–694; Plant Cell Reports (1992) 11:499–505.

Transformation of cultivated tomato is described by McCormick et al., *Plant Cell Reports* (1986) 5:81–89 and Fillatti et al., *Bio/Technology* (1987) 5:726–730.

SUMMARY OF THE INVENTION

Novel DNA constructs and methods for their use are described which are capable of directing transcription of a gene of interest in ovary tissue, particularly early in fruit development. The novel constructs include a vector comprising a transcriptional and translational initiation region obtainable from a gene expressed in ovary tissue and methods of using constructs including the vector for altering fruit phenotype. The fruit may be edible or non-edible. The method includes transfecting a host plant cell of interest with a transcription or expression cassette comprising a promoter which is active in ovary cells prior to, and during, the pollination stage of the fruit, then generating a plant, which is grown to produce fruit having the desired phenotype. Constructs and methods of the subject invention thus find use in modulation of endogenous fruit products, as well as production of exogenous products and in modifying the phenotype of fruit and fruit products. The constructs also find use as molecular probes. In particular, constructs and methods for use in gene expression in cotton embryo tissues are considered herein. By these methods, novel cotton plants and cotton plant parts, such as modified cotton fibers, may be obtained.

DESCRIPTION OF THE DRAWINGS

FIGS. 1A–1B show the DNA sequence of cDNA clone pZ130. The sequences corresponding to the pZ7 cDNA clone are underlined.

FIG. 2A–2C show the sequence of the region of the Calgene Lambda 140 genomic clone that overlaps with the pZ130 cDNA clone (this region is underlined) and a partial sequence of regions 5' and 3' to that region. The start of the pZ130 gene transcript is indicated by the underlined, bold-faced "A" at position 2567. An intron in the gene sequence is indicated by the lower case sequence from position 2702 through position 2921. Sites for common restriction enzymes are indicated.

The symbols in the sequence have the following meaning:

A=adenosine; C=cytosine; G=guanine; T=thymidine or uracil; R=A or G; Y=C or T or U; M=C or A; K=T or U or G; W=T or U or A; S=C or G; N=either C, T, A G or U; B=not A; D=not C; H=not G; V=not T or U.

FIG. 3 shows a restriction map of Calgene Lambda 140. B:BamHI; G:BglII; HindIII; R:EcoRI; S:SalI.

FIG. 4 shows a complete DNA sequence of cDNA clone pZ70. The sequences corresponding to the pZ8 cDNA clone are underlined. The start and end of the mature protein encoded by the pZ70 gene are also indicated.

FIG. 5 shows a restriction map of Calgene Lambda 116. B:BamHI; G:BglII; H:HindIII; P:SphI; R:EcoRI; S:SalI; X:XbaI.

Figure 6A:
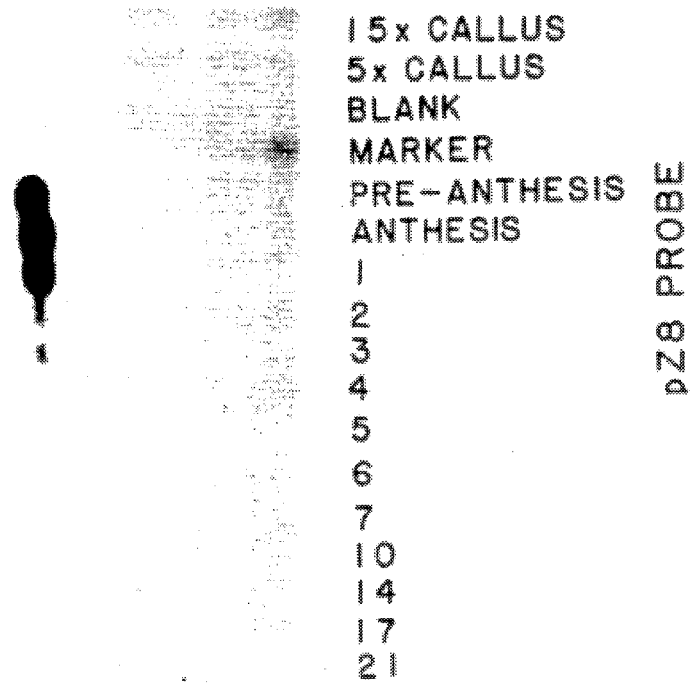
Figure 6B:
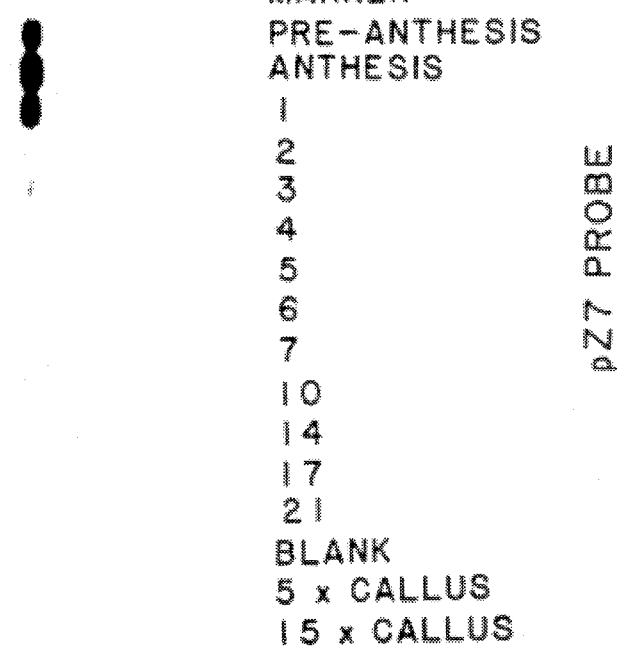
Figure 6C:
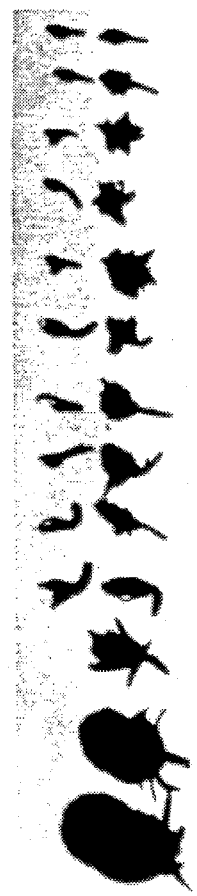

FIG. 6 shows the results of a Northern blot experiment illustrating a developmental time course of pZ7 and pZ8 RNA accumulation. The stages of UC82B fruit development (flowers and ovaries/fruit) are depicted above. Numbers 1 through 21 represent days post flower opening.

Figure 7A:
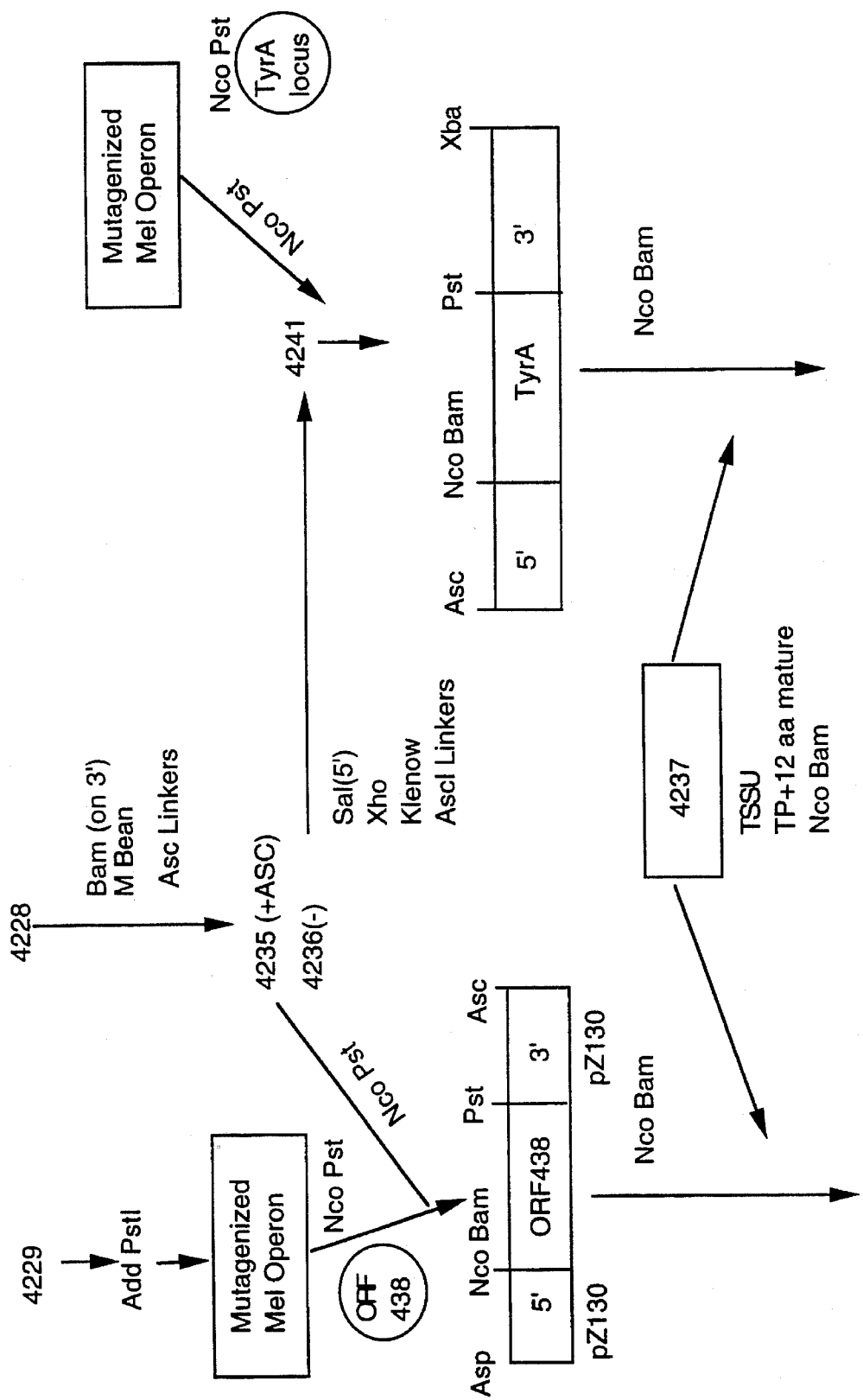
Figure 7B:
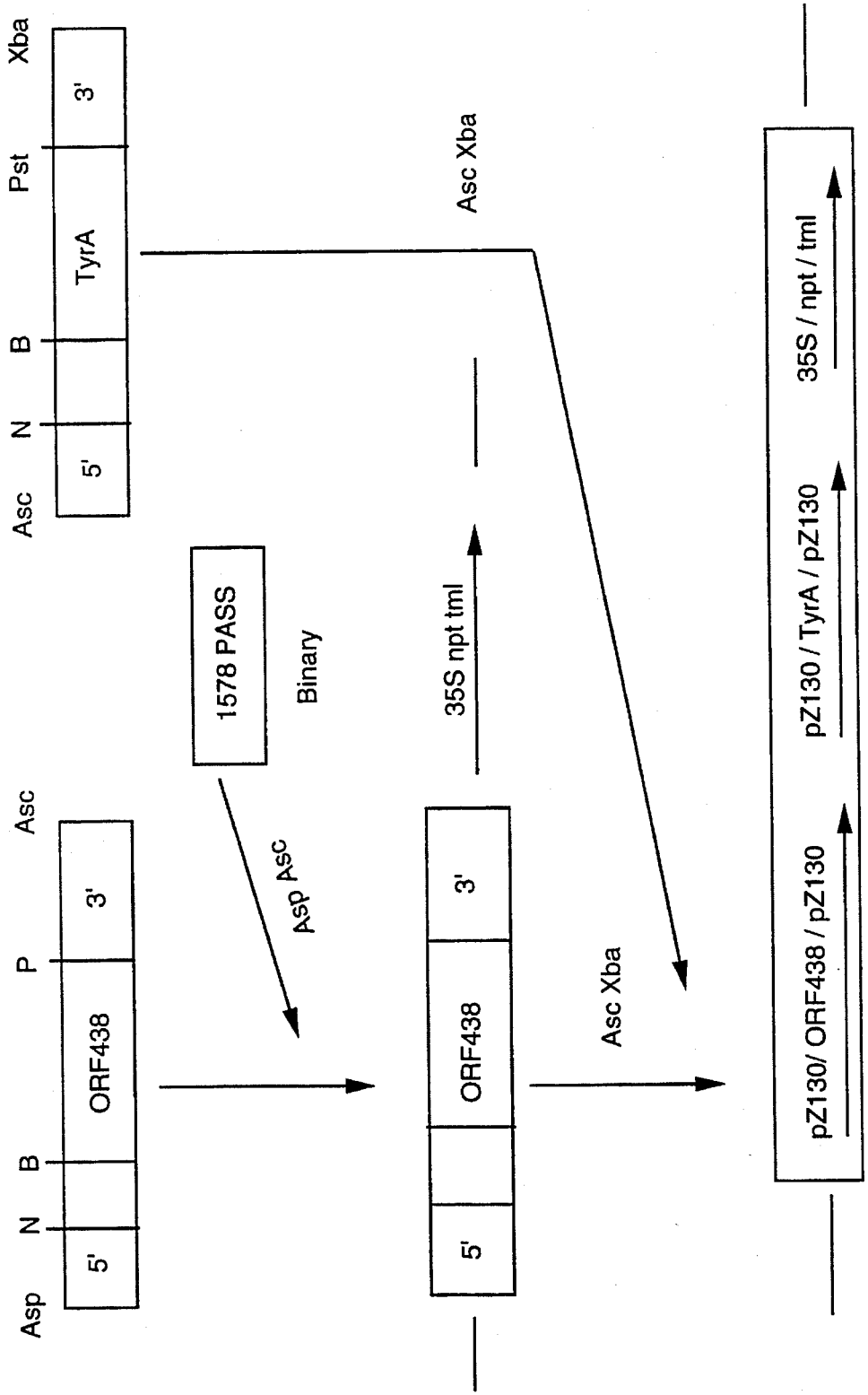

FIG. 7 shows a binary vector for plant transformation to express genes for melanin synthesis.

Figure 8:
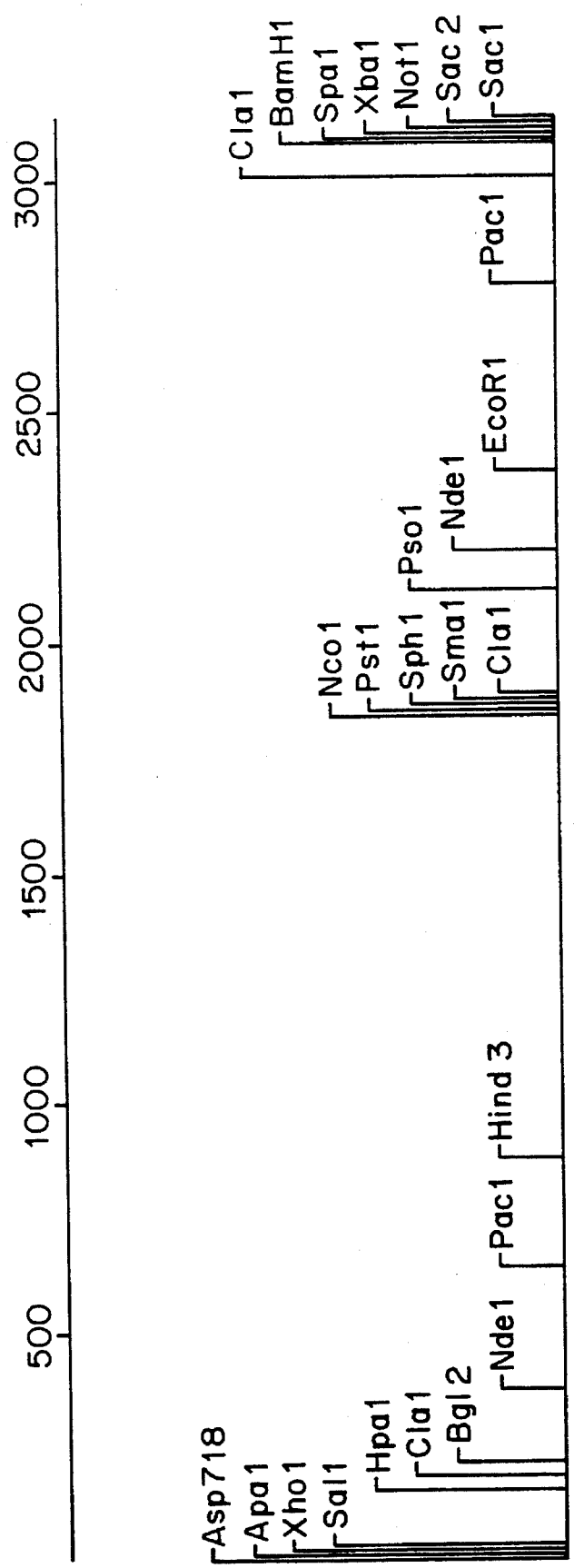

FIG. 8 shows a linker region site map.

DETAILED DESCRIPTION OF THE INVENTION

In accordance with the subject invention, novel constructs and methods for their use are described which may be used as molecular probes or inserted into a plant host to provide for transcription of a nucleotide sequence of interest in ovary cells as compared with other plant cells, generally preferentially in ovary cells to produce cells and plant parts having an altered phenotype. Of particular interest is the period of at least one to three days prior to anthesis through flower senescence.

The constructs include several forms, depending upon the intended use of the construct. Thus, the constructs include vectors, trancriptional cassettes, expression cassettes and plasmids. The transcriptional and translational initiation region (also sometimes referred to as a "promoter,"), preferably comprises a transcriptional initiation regulatory region and a translational initiation regulatory region of untranslated 5' sequences, "ribosome binding sites," responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

The vectors typically comprise a nucleotide sequence of one or more nucleotides and a transcriptional initiation regulatory region associated with gene expression in ovary tissue. A transcriptional cassette for transcription of a nucleotide sequence of interest in ovary tissue will include in the direction of transcription, an ovary tissue transcriptional initiation region and optionally a translational initiation region, a DNA sequence of interest, and a transcriptional and optionally translational termination region functional in a plant cell. When the cassette provides for the transcription and translation of a DNA sequence of interest it is considered an expression cassette. One or more introns may also be present.

Other sequences may also be present, including those encoding transit peptides and secretory leader sequences as desired. The regulatory regions are capable of directing transcription in ovary cells from anthesis through flowering but direct little or no expression after the initial changes which occur at the time surrounding pollination and/or fertilization; transcription from these regulatory regions is not detectable at about three weeks after anthesis. Further, ovary-tissue transcription initiation regions of this invention are typically not readily detectable in other plant tissues. Transcription initiation regions from ovary tissue that are not ovary specific may find special application. Especially preferred are transcription initiation regions which are not found at stages of fruit development other than perianthesis through flowering. Transcription initiation regions capable of initiating transcription in other plant tissues and/or at other stages of ovary development, in addition to the foregoing, are acceptable insofar as such regions provide a significant expression level in ovary tissue at the defined periods of interest and do not negatively interfere with the plant as a whole, and, in particular, do not interfere with the development of fruit and/or fruit-related parts. Also of interest are ovary tissue promoters and/or promoter elements which are capable of directing transcription in specific ovary tissues such as outer pericarp tissue, inner core tissues, integuments, and the like.

Transcriptional initiation regions which are expressible in ovary tissue at or near maximal levels during the period of interest of this invention, generally the flowering period of plant reproductive cycles, are preferred. Of particular interest is the period of at least one to three days prior to anthesis through flower senescence. The transcription level should be sufficient to provide an amount of RNA capable of resulting in a modified fruit. The term "fruit" as used herein refers to the mature organ formed as the result of the development of the ovary wall of a flower and any other closely associated parts. See Weier, T. E., ed., *Botany An Introduction to Plant Biology* (6th ed.) (John Wiley & Sons, 1982); Tootill & Backmore, The Facts on File Dictionary of Botany (Market Home Boob Ltd., 1984). By "modified fruit" is meant fruit having a detectably different phenotype from a nontransformed plant of the same species, for example, one not having the transcriptional cassette in question in its genome.

Of particular interest are transcriptional initiation regions associated with genes expressed in ovary tissue and which are capable of directing transcription at least 24 hours prior to anthesis through flower senescence. The term "anthesis" refers herein to the period associated with flower opening and flowering. The term "flower senescence" refers herein to the period associated with flower death, including the loss of the (flower) petals, etc. Abercrombie, M., et al., *A Dictionary of Biology* (6th ed) (Penguin BooB, 1973). Unopened flowers, or buds, are considered "pre-anthesis." Anthesis begins with the opening of the flower petals, which represents a sexually receptive portion of the reproductive cycle of the plant. Typically, flowering lasts approximately one week in the tested UCB82 tomato variety. In a plant like cotton, flowering lasts approximately two weeks and the fiber develops from the seed coat tissue. It is preferred that the transcriptional initiation regions of this invention do not initiate transcription for a significant time or to a significant degree prior to plant flower budding. Ideally, the level of transcription will be high for at least approximately one to three days and encompass the onset of anthesis ("perianthesis").

It further is desired that the transcriptional initiation regions of this invention show a decreased level of transcriptional activity within 1–3 days after the onset of anthesis which does not increase, and preferably decreases over time. Fertilization of a tomato embryo sac, to produce the zygote that forms the embryo plant, typically occurs 2–3 days after flower opening. This coincides with a decrease in the activity of a transcriptional initiation region of this invention. Thus, it is desired that the transcriptional activity of the promoter of this invention significantly decrease within about two days after the onset of anthesis. Transcriptional initiation regions of this invention will be capable of directing expression in ovary tissue at significant expression levels during the preferred periods described above.

In some embodiments, it will be desired to selectively regulate transcription in a particular ovary tissue or tissues. When used in conjunction with a 5' untranslated sequence capable of initiating translation, expression in defined ovary tissue, including ovary integuments (also known as "ovule epidermal cells"), core or pericarp tissue, and the like, the transcriptional initiation region can direct a desired message encoded by a DNA sequence of interest in a particular tissue to more efficiently effect a desired phenotypic modification. For example, expression in ovary pericarp tissue, also known as the ovary wall and/or ovary core tissue, could result in useful modifications to the edible portions of many fruits, including true berries such as tomato, grape, blueberry, cranberry, currant, and eggplant; stone fruits (drupes), such as cherry, plum, apricot, peach, nectarine and avocado; and compound fruits (druplets), such as raspberry and blackberry. In hespefidium (oranges, citrus), such expression cassettes are expected to be expressed in the "juicy" portion of the fruit. In pepos, (such as watermelon, cantaloupe, honeydew, cucumber, and squash) the equivalent tissue is most likely the inner edible portions. In other fruits, such as legumes, the equivalent tissue is the seed pod.

The modification of analogous structures of non-edible fruit may also be of interest. Thus, of special interest are transcription initiation regions expressible in at least ovary outer pericarp tissue. For example, in cotton the analogous ovary structure is the burr of the cotton boll, in rapeseed it is the seed pod. In a like manner, regulating expression in ovary integuments and/or core tissue may result in useful modifications to the analogous fruit and related structures evolving there from, for example seed coat hairs, such as cotton fibers. Cotton fiber is a differentiated single epidermal cell of the outer integument of the ovule. It has four distinct growth phases; initiation, elongation (primary cell wall synthesis), secondary cell wall synthesis, and maturation. Initiation of fiber development appears to be triggered by hormones. The primary cell wall is laid down during the elongation phase, lasting up to 25 days postanthesis (DPA). Synthesis of the secondary wall commences prior to the cessation of the elongation phase and continues to approximately 40 DPA, forming a wall of almost pure cellulose. In addition to ovary tissue promoters, transcriptional initiation regions from genes expressed preferentially in seed tissues, and in particular seed coat tissues, are also of interest for applications where modification of cotton fiber cells is considered.

An example of a gene which is expressed at high levels in Brassica seed coat cells is the EA9 gene described in EPA 0 255 378. The nucleic acid sequence of a portion of the EA9 cDNA is provided therein, and can be used to obtain corresponding sequences, including the promoter region. An additional seed gene which is expressed in seed embryo and seed coat cells is the Bce4 Brassica gene. The promoter region from this gene also finds use in the subject invention; this gene and the corresponding promoter region are described in WO 91/13980, which was published Sep. 19, 1991. Fiber specific proteins are developmentally regulated. Thus, transcriptional initiation regions from proteins expressed in fiber cells are also of interest. An example of a developmentally regulated fiber cell protein, is E6 (John and Crow Proc. Nat. Acad. Sci. (USA)(1992) 89:5769–5773). The E6 gene is most active in fiber, although low levels of transcripts are found in leaf, ovule and flower.

To obtain a specifically derived transcriptional initiation region, the following steps may be employed. Messenger RNA (mRNA) is isolated from tissue of the desired developmental stage. This mRNA is then used to construct cDNA clones which correspond to the mRNA population both in terms of primary DNA sequence of the clones and in terms of abundance of different clones in the population. mRNA is also isolated from tissue of a different developmental stage in which the target gene should not be expressed (alternate tissue). Radioactive cDNA from the desired tissue and from the alternate tissue is used to screen duplicate copies of the cDNA clones. The preliminary screen allows for classification of the cDNA clones as those which correspond to mRNAs which are abundant in both tissues; those which correspond to mRNAs which are not abundant in either tissue; those which correspond to mRNAs which are abundant in one tissue and relatively non-abundant in the other. Clones are then selected which correspond to mRNAs that are abundant only in the desired tissue and then these selected clones are further characterized.

Since the hybridization probe for the preliminary screen outlined above is total cDNA from a particular tissue, it hybridizes primarily to the most abundant sequences. In order to determine the actual level of expression, particularly in tissue where the mRNA is not as abundant, the cloned sequence is used as a hybridization probe to the total mRNA population(s) of the desired tissue(s) and various undesired tissue(s). This is most commonly done as a Northern blot which gives information about both the relative abundance of the mRNA in particular tissues and the size of the mRNA transcript.

It is important to know whether the abundance of the mRNA is due to transcription from a single gene or whether it is the product of transcription from a family of genes. This can be determined by probing a genomic Southern blot with the cDNA clone. Total genomic DNA is digested with a variety of restriction enzymes and hybridized with the radioactive cDNA clone. From the pattern and intensity of the hybridization, one can distinguish between the possibilities that the mRNA is encoded either by one or two genes or by a large family of related genes. It can be difficult to determine which of several cross-hybridizing genes encodes the abundantly expressed mRNA found in the desired tissue. For example, tests indicate that pZ130 (see Example 4) is a member of a small gene family however, the pZ7 probe is capable of distinguishing pZ130 from the remainder of the family members.

The cDNA obtained as described can be sequenced to determine the open reading frame (probable protein-coding region) and the direction of transcription so that a desired target DNA sequence later can be inserted at the correct site and in the correct orientation into a transcription cassette. Sequence information for the cDNA clone also facilitates characterization of corresponding genomic clones including mapping and subcloning as described below. At the same time, a genomic library can be screened for clones containing the complete gene sequence including the control region flanking the transcribed sequences. Genomic clones generally contain large segments of DNA (approximately 10–20 kb) and can be mapped using restriction enzymes, then subcloned and partially sequenced to determine which segments contain the developmentally regulated gene.

Using the restriction enzyme map and sequence infomarion, plasmids can be designed and constructed which have the putative ovary gene or other desired promoter regions attached to genes which are to be expressed in ovary and/or other desired tissue, particularly ovary-derived tissue. These hybrid constructions are tested for their pattern of expression in transformed, regenerated plants to be sure that the desired timing and/or tissue expression and/or the overall level of expression has been maintained successfully when the promoter is no longer associated with the native open reading frame. Using the method described above, several transcriptional regulatory regions have been identified. One example is the tomato-derived transcriptional initiation region which regulates expression of the sequence corresponding to the pZ130 cDNA clone. Sequences hybddizable to the pZ130 clone, for example, probe pZ7, show abundant mRNA, especially at the early stages of anthesis. The message is expressed in ovary integument and ovary outer pericarp tissue and is not expressed, or at least is not readily detectable, in other tissues or at any other stage of fruit development. Thus, the pZ130 transcriptional initiation region is considered ovary-specific for purposes of this invention. FIG. 1 provides the DNA sequence of cDNA clone pZ130. The native function of the amino acid sequence encoded by the structural gene comprising pZ130 is unknown.

Downstream from, and under the regulatory control of, the ovary tissue transcriptional/translational initiation control region is a nucleotide sequence of interest which provides for modification of the phenotype of structures maturing from ovary tissue, such as fruit or fiber. The nucleotide sequence may be any open reading frame encoding a polypeptide of interest, for example, an enzyme, or a sequence complementary to a genomic sequence, where the genomic sequence may be an open reading frame, an intron, a noncoding leader sequence, or any other sequence where the complementary sequence inhibits transcription, messenger RNA processing, for example, splicing, or translation. The nucleotide sequences of this invention may be synthetic, naturally derived, or combinations thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest. Phenotypic modification can be achieved by modulating production either of an endogenous transcription or translation product, for example as to the amount, relative distribution, or the like, or an exogenous transcription or translation product, for example to provide for a novel function or products in a transgenie host cell or tissue. Of particular interest are DNA sequences encoding expression products associated with the development of plant fruit, including genes involved in metabolism of cytokinins, auxins, ethylene, abscissic acid, and the like. Methods and compositions for modulating cytokinin expression are described in U.S. Pat. No. 5,177,307, which disclosure is hereby incorporated by reference. Alternatively, various genes, from sources including other eukaryotic or prokaryotic cells, including bacteria, such as those from *Agrobacterium tumefaciens* T-DNA auxin and cytokinin biosynthetic gene products, for example, and mammals, for example inteferons, may be used.

Other phenotypic modifications include modification of the color of plant parts developing from ovary integuments and/or core tissue, for example seed coat hairs, such as cotton fibers. Of interest are genes involved in production of melanin and genes involved in the production of indigo. Melanins are dark brown pigments found in animals, plants and microorganisms, any of which may serve as a source for sequences for insertion into the constructs of the present invention. Specific examples include the tyrosinase gene which can be cloned from *Streptomyces antibioticus*. The ORF438 encoded protein in *S. antibioticus* also is necessary for melanin production, and may provide a copper donor function. In addition, a tyrosinase gene can be isolated from any organism which makes melanin. The gene can be isolated from human hair, melanocytes or melanomas, cuttle fish and red roosters, among others. See, for example, EP Application No. 89118346.9 which discloses a process for producing melanins, their precursors and derivatives in microorganisms. Also, See, Bernan et al. Gene (1985) 37:101–110; and della-Cioppa et al. Bio/Technology (1990) 8:634–638.

Indigo may be obtained by use of genes encoding a mono-oxygenase such as xylene oxygenase which oxidizes toluene and xylene to (methyl) benzyl alcohol and also transforms indole to indigo. Cloning of the xylene oxygenase gene and the nucleotide and amino acid sequences are described in unexamined Japanese Patent Application Kokai:2-119777, published May 7, 1990. A dioxygenase such as naphthalene dioxygenase which also converts indole to indigo finds use; the naphthalene dioxygenase gene nahA is described in Science (1983) 222:167. For cloning, nucleotide sequence in characterization of genes encoding naphthalene dioxygenase of *Pseudomonas putida*. See, Kurkela et al. Gene (1988) 73:355–362. A tryptophanase gene sequence can be used in conjunction with an oxygenase to increase the amount of indole available for conversion to indigo. Sources of tryptophanase gene sequences include *E. coli* (see, for example, Deeley et al. (1982) *J. Bacteriol.* 151:942–951).

Also of interest are genes involved in production of colored pigments in plant tissues, such as the Maize A1 gene which encodes a dihydroflavonol reductase, an enzyme of the anthocyanin pigmentation pathway. In cells that express the A1 gene, dihydrokempferol is converted to 2-8 alkylleucopelargonidin, which may be further metabolized to pelargonidin pigment by endogenous plant enzymes. Other anthocyanin or flavonoid type pigments may also be of interest for modification of cotton cell fibers. For a review of plant flower color manipulation, see van Tunen et al. (in Plant Biotechnology Series, Volume 2 (1990) Developmental Regulation of Plant Gene Expression, D. Grierson ed.). Although cotton fibers in commercially grown varieties are primarily whim in color, other naturally occurring cotton varieties have brown or reddish-brown fibers. Also a cotton line containing green colored fibers has been identified. The existence of these colored cotton lines suggests that the precursors required for the anthocyanin pigment pathways are present in cotton fibers cells, thus allowing further color phenotype modifications.

For some applications, it is of interest to modify other aspects of structures developing from the ovary integument and related structures. For example, it is of interest to modify various aspects of cotton fibers, such as strength or texture of a fiber. Thus, the appropriate gene may be inserted in the constructs of the invention, including genes for PHB biosynthesis (See, Peoples et al. *J. Biol. Chem.* (1989) 264:15298–15303 and Ibid. 15293–15397; Saxena, *Plant Molecular Biology* (1990) 15:673–683, which discloses cloning and sequencing of the cellulose synthase catalytic subunit gene; and Bowen et al. *PNAS* (1992) 89:519–523 which discloses chitin synthase genes of *Saccharomyces cerevisiae* and *Candida albicans*.

Transcriptional cassettes may be used when the transcription of an anti-sense sequence is desired. When the expression of a polypeptide is desired, expression cassettes providing for transcription and translation of the DNA sequence of interest will be used. Various changes are of interest; these changes may include modulation (increase or decrease) of formation of particular saccharities, hormones, enzymes, or other biological parameters. These also include modifying the composition of the final fruit or fiber, that is changing the ratio and/or mounts of water, solids, fiber or sugars. Other phenotypic properties of interest for modification include response to stress, organisms, herbicides, brushing, growth regulators, and the like. These results can be achieved by providing for reduction of expression of one or more endogenous products, particularly an enzyme or cofactor, either by producing a transcription product which is complementary (anti-sense) to the transcription product of a native gene, so as to inhibit the maturation and/or expression of the transcription product, or by providing for expression of a gene, either endogenous or exogenous, to be associated with the development of a plant fruit.

The termination region which is employed in the expression cassette will be primarily one of convenience, since the termination regions appear to be relatively interchangeable. The termination region may be native with the transcriptional initiation region, may be native with the DNA sequence of interest, may be derived from another source. The termination region may be naturally occurring, or wholly or partially synthetic. Convenient termination regions are available from the Ti-plasmid of *A. tumefaciens*, such as the octopine synthase and nopaline synthase termination regions. In some embodiments, it may be desired to use the 3' termination region native to the ovary tissue transcription initiation region used in a particular construct.

In some instances, it may be useful to include additional nucleotide sequences in the constructs to provide for targeting of a particular gene product to specific cell organelles. For example, where coding sequences for synthesis of aromatic colored pigments are used in a constructs, particularly coding sequences for enzymes which have as their substrates aromatic compounds such tyrosine and indole, it is preferable to include sequences which provide for delivery of the enzyme into plastids, such as an SSU transit peptide sequence.

For melanin production, the tyrosinase and ORF438 genes from *Streptomyces antibioticus* (Berman et al. (1985) 37:101–110) are provided in cotton fiber cells for expression from a pZ130 promoter. In Streptomyces, the ORF438 and tyrosinase proteins are expressed from the same promoter region. For expression from constructs in a transgenie plant genome, the coding regions may be provided under the regulatory control of separate promoter regions. The promoter regions may be the same or different for the two genes. Alternatively, coordinate expression of the two genes from a single plant promoter may be desired. Constructs for expression of the tyrosinase and ORF438 gene products from pZ130 promoter regions are described in detail in the following examples. Additional promoters may also be desired, for example plant viral promoters, such as CaMV 35s, can be used for constitutive expression of one of the desired gene products, with the other gene product being expressed in cotton fiber tissues from the pZ130 promoter. In addition, the use of other plant promoters for expression of genes in cotton fibers is also considered, such as the Brassica seed promoters and the E6 gene promoter discussed above. Similarly, other constitutive promoters may also be useful in certain applications, for example the mas, Mac or DoubleMac, promoters described in U.S. Pat. No. 5,106,739 and by Comai et al., *Plant Mol. Biol.* (1990) 15:373–381). When plants comprising multiple gene constructs are desired, for example plants expressing the melanin genes, ORF438 and tyrosinase, the plants may be obtained by co-transformation with both constructs, or by transformation with individual constructs followed by plant breeding methods to obtain plants expressing both of the desired genes.

The various constructs normally will be joined to a marker for selection in plant cells. Conveniently, the marker may be resistance to a biocide, particularly an antibiotic, such as kanamycin, G418, bleomycin, hygromycin, chloramphenicol, or the like. The particular marker employed will be one which will allow for selection of transformed cells as compared to cells lacking the DNA which has been introduced. Components of DNA constructs including transcription cassettes of this invention may be prepared from sequences which are native (endogenous) or foreign (exogenous) to the host. By foreign is intended that the sequence is not found in the wild-type host into which the construct is introduced. Heterologous constructs will contain at least one region which is not native to the gene from which the ovary tissue transcription initiation region is derived.

In preparing the constructs, the various DNA fragments may be manipulated, so as to provide for DNA sequences in the proper orientation and, as appropriate, in proper reading frame for expression; adapters or linkers may be employed for joining the DNA fragments or other manipulations may be involved to provide for convenient restriction sites, removal of superfluous DNA, removal of restriction sites, or the like. In vitro mutagenesis, primer repair, restriction, annealing, resection, ligation, or the like may be employed, where insertions, deletions or substitutions, e.g. transitions and transversions, may be involved. Conveniently, a vector or cassette may include a multiple cloning site downstream from the ovary-related transcription initiation region, so that the construct may be employed for a variety of sequences in an efficient manner.

In carrying out the various steps, cloning is employed, so as to amplify the amount of DNA and to allow for analyzing the DNA to ensure that the operations have occurred in proper manner. By appropriate manipulations, such as restriction, chewing back or filling in overhangs to provide blunt ends, ligation of linkers, or the like, complementary ends of the fragments can be provided for joining and ligation. A wide variety of cloning vectors are available, where the cloning vector includes a replication system functional in *E. coli* and a marker which allows for selection of the transformed cell. Illustrative vectors include pBR322, pUC series, M13mp series, pACYC184, etc. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence. Each of the partial constructs may be cloned in the same or different plasmids.

A variety of techniques are available and known to those skilled in the art for introduction of constructs into a plant cell host. These techniques include transfection with DNA employing *A. tumefaciens* or *A. rhizogenes* as the transfecting agent, protoplast fusion, injection, electroporation, particle acceleration, etc. For transformation with Agrobacterium, plasmids can be prepared in *E. coli* which contain DNA homologous with the Ti-plasmid, particularly T-DNA. The plasmid may or may not be capable of replication in Agrobacterium, that is, it may or may not have a broad spectrum prokaryotic replication system such as does, for example, pRK290, depending in part upon whether the transcription cassette is to be integrated into the Ti-plasmid or to be retained on an independent plasmid. The Agrobacterium host will contain a plasmid having the vir genes necessary for transfer of the T-DNA to the plant cell and may or may not have the complete T-DNA. At least the fight border and frequently both the fight and left borders of the T-DNA of the Ti- or Ri-plasmids will be joined as flanking regions to the transcription construct. The use of T-DNA for transformation of plant cells has received extensive study and is amply described in EPA Serial No. 120,5 16, Hoekema, In: The Binary Plant Vector System Offset-drukkerij Kanters B. V., Alblasserdam, 1985, Chapter V, Knauf, et al., Genetic Analysis of Host Range Expression by Agrobacterium, In: Molecular Genetics of the Bacteria-Plant Interaction, Puhler, A. ed., Springer-Verlag, N.Y., 1983, p. 245, and An, et al., *EMBO J.* (1985) 4:277–284.

For infection, particle acceleration and electroporation, a disarmed Ti-plasmid lacking particularly the tumor genes found in the T-DNA region) may be introduced into the plant cell. By means of a helper plasmid, the construct may be transferred to the *A. tumefaciens* and the resulting transfected organism used for transfecting a plant cell; explants may be cultivated with transformed *A. tumefaciens* or *A. rhizogenes* to allow for transfer of the transcription cassette to the plant cells. Alternatively, to enhance integration into the plant genome, terminal repeats of transposons may be used as borders in conjunction with a transposase. In this situation, expression of the transposase should be inducible, so that once the transcription construct is integrated into the genome, it should be relatively stably integrated. Transgenic plant cells are then placed in an appropriate selective medium for selection of transgenic cells which are then grown to callus, shoots grown and plantlets generated from the shoot by growing in rooting medium.

To confirm the presence of the transgenes in transgenic cells and plants, a Southern blot analysis can be performed using methods known to those skilled in the art. Expression products of the transgenes can be detected in any of a variety of ways, depending upon the nature of the product, and include immune assay, enzyme assay or visual inspection, for example to detect pigment formation in the appropriate plant part or cells. Once transgenic plants have been obtained, they may be grown to produce fruit having the desired phenotype. The fruit or fruit parts, such as cotton fibers may be harvested, and/or the seed collected. The seed may serve as a source for growing additional plants having the desired characteristics. The terms transgenic plants and transgenic cells include plants and cells derived from either transgenic plants or transgenic cells.

The various sequences provided herein may be used as molecular probes for the isolation of other sequences which may be useful in the present invention, for example, to obtain related transcriptional initiation regions from the same or different plant sources. Related transcriptional initiation regions obtainable from the sequences provided in this invention will show at least about 60% homology, and more preferred regions will demonstrate an even greater percentage of homology with the probes. Of particular importance is the ability to obtain related transcription initiation control regions having the timing and tissue parameters described herein. For example, using the probe pZ130, at least 7 additional clones, have been identified, but not further characterized. Thus, by employing the techniques described in this application, and other techniques known in the art (such as Maniatis, et al., *Molecular Cloning; A Laboratory Manual* (Cold Spring Harbor, N.Y.) 1982), other transcription initiation regions capable of directing ovary tissue transcription as described in this invention may be determined. The constructs can also be used in conjunction with plant regeneration systems to obtain plant cells and plants; the constructs may also be used to modify the phenotype of a fruit and fruits produced thereby.

For cotton applications, various varieties and lines of cotton may find use in the described methods. Cultivated cotton species include *Gossypium hirsutum* and *G. babadense* (extra-long stable, or Pima cotton), which evolved in the New World, and the Old World crops *G. herbaceum* and *G. arborcure*.

The following examples are offered by way of illustration and not by limitation.

EXPERIMENTAL

The following deposits have been made at the American Type Culture Collection (ATCC) (12301 Parklawn Drive, Rockville, Md. 20852). Bacteriophage Calgene Lambda 116 and Calgene Lambda 140, each containing a transcription initiation region of this invention, were deposited on Jul. 13, 1989 and were given accession numbers 40632 and 40631, respectively.

EXAMPLE 1

Construction of Pre-Anthesis Tomato Ovary cDNA Banks and Screening for Ovary-Specific Clones cDNA Library Preparation

Tomato plants (*Lycopersicon esculentum* cv UC82B) were grown under greenhouse conditions. Poly(A)+RNA was isolated as described by Mansson et al., *Mol. Gen.*

*Genet.* (1985) 200:356–361. The synthesis of cDNA from poly(A)+RNA, prepared from ovaries of unopened tomato flowers (pre-anthesis stage), was carried out using the BRL cDNA Cloning Kit following the manufacturer's instructions (BRL; Bethesda, Md.). Addition of restriction endonuclease EcoRI linkers (1078, New England Biolabs; Beverly, Mass.) to the resulting double-stranded cDNA was accomplished by using the procedures described in Chapter 2 of *DNA Cloning Vol. I: A Practical Approach*, Glover, ed., (IRL Press, Oxford 1985). Cloning the cDNA into the EcoRI site of the phage Lambda ZAP (Stratagene; La Jolla, Calif.) and packaging the resulting recombinant phage (using Giga-Pack Gold, Stratagene) was carried out as described in the respective commercial protocols.

Two cDNA libraries were prepared as described above from the same pre-anthesis stage mRNA. For the second library, which contained significantly longer cDNA than the first, the poly(A)+RNA sample was run through an RNA spin column (Boehringer Mannheim Biochemicals; Indianapolis, Ind.), following the manufacturer's directions, prior to the cloning procedures.

cDNA Library Screening

The first cDNA library was screened by differential hybridization using $^{32}$P-labelled cDNA probes made from pre-anthesis mRNA, leaf mRNA and young seedling mRNA. Clones were selected based on hybridization to only preanthesis mRNA. The cDNAs corresponding to the selected Lambda ZAP (Stratagene) clones were excised from the phage vector and propagated as plasmids (following the manufacturer's instructions).

From an initial screen of 1000 cDNAs, 30 selected clones falling into five classes based on the sequences of their cDNA inserts were isolated. Two clones, clones pZ7 and pZ8, were selected for further study. The DNA sequences of pZ7 and pZ8 are shown as the underlined portions of FIGS. 1 and 4, respectively.

Several thousand recombinant clones from the second cDNA library were screened by plaque hybridization (as described in the Stratagene Cloning Kit Instruction Manual) with a mixture of radiolabelled DNA probes. Screening of approximately three thousand recombinant clones from the second library with the pZ7 and pZ8 DNA probes yielded selection of fourteen clones which had intense hybridization signals. The clones selected were excised from the phage vector and propagated as plasmids. DNA was isolated from each clone, cut with the restriction endonuclease EcoRI, then electrophoresed through a 0.7% agarose gel. Duplicate blot hybridizations were performed as described in Maniatis et al., *Molecular Cloning: A Laboratory Manual* (Cold Spring Harbor, N.Y., 1982) with radiolabelled probes representing the genes of interest (pZ7 and pZS). Seven clones which hybridized to pZ7 and three clones which hybridized to pZ8 were selected. The longest of these for each probe, pZ130 (pZ7-hybridizing) and pZ70 (pZ8-hybridizing), were characterized further and used in additional experiments.

EXAMPLE 2

Analysis of cDNA Clones

Northern Analysis

Tissue-specificity of the cDNA clones was demonstrated as follows: RNA was isolated from 1, 2, 3, 4, 5, 6, 7, 10, 14, 17 and 21 day post-anthesis, anthesis and pre-anthesis stage tomato ovaries, tomato leaves and unorganized tomato callus using the method of Ecker and Davis, *Proc. Natl. Acad. Sci. USA*, 84:5203 (1987) with the following modifications. After the first precipitation of the nucleic acid, the pellets were resuspended in 2 ml of diethylpyrocarbonate (DEP-)treated water on ice. The solutions were brought to 1 mM $MgCl_2$ and ¼ volume of 8 M LiCl was added. The samples were mixed well and stored at 4° C. overnight. The samples were then centrifuged at 8,000 RPM for 20 min. at 4° C. The pellets were dried, resuspended in DEP-treated water on ice as before and ethanol precipitated once more. The RNAs were electrophoresed on formaldehyde/agarose gels according to the method described by Fourney et al., *Focus* (1988) 10:5–7, immobilized on Nytran membranes (Schleicher & Schuell; Keene, N.H.) and hybridized with $^{32}$P-labelled probes.

Based upon the Northern analysis with a 32P-labelled pZ7 EcoRI insert DNA or a pZ8 EcoRI insert DNA, it is clear that both of these genes are most highly expressed at anthesis in tomato variety UC82B and somewhat less highly expressed prior to and a day following the opening of the flower. FIG. 6 shows tomato flowers at various stages of development and immediately below, a representative ovary dissected from a flower at the same stage of development. As seen in FIG. 6, by two days after the onset of anthesis, the expression of both genes had dropped off dramatically. The size of the mRNA species hybridizing to the pZ7 probe was approximately 800 nt and to the pZ8 probe approximately 500 nt.

From two days post-anthesis, pZ8 RNA accumulation was apparently maintained at a relatively low level while pZ7 RNA accumulation continued to drop off steadily until, by three weeks post-anthesis, it was undetectable by this analysis. pZ8 RNA accumulation was not detectable by the method described above in RNA samples isolated from tomato fruit older than the immature green stage of fruit ripening. No RNA hybridizing to pZ7 or pZ8 was found in callus tissue; no RNA hybridizing to pZ7 was found in leaf tissue; on longer exposures a barely detectable hybridization signal for pZ8 was seen in leaf RNA.

Expression Level

Message abundance corresponding to the cDNA probes was determined by comparing the hybridization intensity of a known amount of RNA synthesized in vitro from the clones (using T7 or T3 RNA polymerase in the Riboprobe System (Promega)) to RNA from anthesis stage and three week old tomato ovaries. This analysis indicated that pZ7 and pZ8 cDNAs represent abundant RNA classes in anthesis-stage tomato ovaries, being approximately 5% and 2% of the message, respectively.

Cellular Specificity

The cellular specificity of the cDNA probes may be demonstrated using the technique of in situ hybridization. Preanthesis stage UC82B tomato ovaries were fixed overnight in a 4% paraformaldehyde, phosphate buffered saline (PBS), 5 mM $MgCl_2$ solution, pH 7.4 (PBS is 10 mM phosphate buffer, pH 7.4, 150 mM NaCl) (Singer et al., Biotechniques (1986) 4:230–250). After fixation, the tissue was passed through a graded tertiary butyl alcohol CrBA) series, starting at 50% alcohol, infiltrated with Paraplast and cast into paraffin blocks for sectioning (Berlyn and Miksche, *Botanical Microtechnique and Cytochemistry*, (1976) Iowa). Embedded ovaries were transversely cut, 8 μm thick sections, on a Reichert Histostat rotary microtome. Paraffin ribbons holding 5–7 ovary sections were affixed to gelatinochrom alum subbed slides (Berlyn and Miksche (1976) supra) and held in a dust-free box until in situ hybridizations were performed. Slides ready to be hybridized were deparaffinized in xylene and rehydrated by passing through an ethanol hydralion series as described in Singer et al., supra (1986).

A 2X hybridization mix was made consisting of 100 µl 20X SSC, 20 µl 10% BSA, 100 µl 750 mM DTT, 200 µl 50% dextran sulfate, 50 µl RNasin, and 30 µl sterile water. Sense and antisense $^{35}$S-RNA probes were generated from cDNAs of interest using T3 and T7 RNA polymerases in vitro transcription (Riboprobe Promega Biotec or Stratagene) reactions following the manufacturer's protocol. 2.5 µl tRNA (20 mg/ml), 2.5 µl salmon sperm DNA (10 mg per ml) and 4 ×10$^6$ cpm/probe were dried down using a lyophilizer. This mix was then resuspended in 25 µl 90% formamide containing 25 µl 2X hybridization mix per slide. 40 µl of this hybridization mix was placed on each slide. A cover slip was placed over the sections and edges sealed with robber cement. Slides were placed in slide holders inside a glass slide box, covered, and placed in a 37° C. dry oven overnight to hybridize. Posthybridization treatments were as described in Singer et al., (1986), supra.

Autoradiography was performed as described in *KODAK Materials for Light Microscope* (KODAK (1986); Rochester, N.Y.) using liquid emulsion NTB-3. Slides are left to expose in a light-fight box for approximately two weeks. After developing the autoradiographic slides, sections were stained in 0.05% toluidine blue and then dehydrated through a graded alcohol series; xylene:100% ethanol, 1:1, followed by 2 changes of 100% xylene, five minutes in each solution. Coverslips were mounted with Cytoseal (VWR; San Francisco, Calif.) and left on a slide warmer until dry (45°–50° C., 1–2 days). Autoradiographic slides were then ready for microscopic examination.

When pre-anthesis tomato ovaries were hybridized to sense and antisense $^{35}$S-pZ7 RNA, the antisense transcripts hybridized specifically to the outer pericarp region of the ovary and to the outer region of the ovules (the integuments). The sense transcripts (negative control) showed no hybridization. When preanthesis tomato ovaries were hybridized to sense and antisense $^{35}$S-pZ8 RNA, the antisense transcript hybridized specifically to the inner core region of the ovary and to the outer region of the ovules. The sense transcripts showed no hybridization.

In summary, the mRNA transcripts encoded by the genes corresponding to pZ7 and pZ8 were abundantly expressed during a very specific stage of tomato fruit development, primarily at anthesis and at a day prior to and after the opening of the flower. The transcripts additionally were expressed in a specific subset of tomato ovary cell types during that stage of development particularly in the integuments (pZ7 and pZS) as well as the ovarian outer pericarp (pZ7) and inner core region (pZ8).

EXAMPLE 3

Sequencing of pZ130 and pZ70 cDNA Clones

The complete DNA sequences of the cDNA pZ130 and pZ70 clones were determined using the Sanger et at. (1971) dideoxy technique. The DNA sequences of both pZ130 and pZ70 were translated in three frames. The sequences, including the longest open reading frame for each, are shown in FIG. 1 (pZ130) and FIG. 4 (pZ70).

EXAMPLE 4

Analysis of Gene Family

Southern analysis was performed as described by Maniatis et at., supra, (1982). Total tomato DNA from cultivar UC82B was digested with BamHI, EcoRI and HindIII, separated by agarose gel electrophoresis and transferred to nitrocellulose. Southern hybridization was performed using $^{32}$P-labelled probes produced by random priming of pZ130 or pZ70. A simple hybridization pattern indicated that the genes encoding pZ130 and pZ70 are present in a few or perhaps only one copy in the tomato genome.

Additional analysis, using a pZ130 hybridization probe to hybridize to tomato genomic DNA digested with the restriction endonuclease BglII, indicated that this gene is actually a member of a small (approximately 5–7 member) family of genes. The original pZ7 cDNA clone, consisting of sequences restricted to the 3'-untranslated region of the longer pZ130 clone, however, hybridizes intensely only to one band and perhaps faintly to a second band based on Southern analysis using BglII digested tomato genomic DNA.

EXAMPLE 5

Preparation of Genomi$_c$Clones pZ130 and pZ70

Two genomic clones, one representing each of cDNA clones pZ130 and pZ70, were obtained as follows. A genomic library constructed from DNA of the tomato cultivar UC82B, partially digested with the restriction endonuclease Sau3A, was established in the lambda phage vector, lambda-FIX according to the manufacturer's instructions (Stratagene; La Jolla, Calif.). This library was screened using $^{32}$P-labelled pZ130 and pZ70 as probes. A gertomit clone containing approximately 14.5 kb of sequence from the tomato genome which hybridized to pZ70 was isolated. The region which hybridizes to the pZ70 probe was found within the approximately 2 kb XbaI-HindIII restriction fragment of Calgene Lambda 116 (See FIG. 5). A second genomic clone, containing approximately 13 kb of sequence from the tomato genome and hybridizing to pZ130 (and pZ7) was isolated. The region which hybridized to the pZ130 probe was found within the larger EcoRIHindIII restriction fragment of Calgene Lambda 140 (See FIG. 3).

Preparation of pCGN2015 pCGN2015 was prepared by digesting pCGN565 with HhaI, blunting with mung bean nuclease, and inserting the resulting fragment into an EcoRV digested BluescriptKSM13-(Stratagene) vector to create pCGN2008. pCGN2008 was digested with EcoRI and HindIII, blunted with Klenow, and the 1156 bp chloramphenicol fragment isolated. BluescfiptKSM13+(Stratagene) was digested with DraI and the 2273 bp fragment isolated and ligated with the pCGN2008 chloramphenicol fragment creating pCGN2015.

Preparation Of pCGN2901/pCGN2902 pCGN2901 contains the region surrounding the pZ7-hybridizing region of the pZ130 genomic clone, including approximately 1.8 kb in the 5' direction and approximately 4 kb in the 3'-direction. To prepare pCGN2901, Calgene Lambda 140 was digested with SalI and the resulting fragment which contains the pZ7-hybridizing region was inserted into pCGN2015, at the pCGN2015 unique SalI site, to create pCGN2901.

pCGN2902 contains the other SalI fragment (non-pZ7-hybridizing) of the pZ130 genome derived from SalI digestion of Calgene Lambda 140, also put into a pCGN2015 construct.

EXAMPLE 6

Preparation of a pZ130 Expression Construct

Plasmid DNA isolated from pCGN2901 was digested to completion with NcoI and then treated with exonuclease isolated from mung bean (Promega, Madison, Wis.) to eliminate single-stranded DNA sequences including the ATG sequence making up a portion of the NcoI recognition sequence. The sample was then digested to completion with SacI. The resulting 1.8 kb (approximate) 5' SacI to NcoI fragment was then inserted into a pUC-derived ampicillin-resistant plasmid, pCGP261 (described below), that had been prepared as follows. pCG261 was digested to completion with XbaI, the single-stranded DNA sequences were filled in by treatment with the Klenow fragment of DNA polymerase I, and the pCGP261 DNA redigested with SacI. The resulting expression construct contained, in the 5' to 3' direction of transcription, an ovary tissue promoter derived from Lambda 140, a tmr gene and tmr 3'-transcriptional termination region.

The plasmid pCGP261 contains the sequences from position 8,762 through 9,836 from the *Agrobacterium tumefaciens* octopine Ti plasmid pTi15955 (as sequenced by Barker et al., *Plant Molec. Biol.* (1983) 2:335–350). This region contains the entire coding region for the genetic locus designated tmr which encodes isopentenyltransferase (Akiyoshi et al., *PNAS* (1984) 81:4776–4780), 8 bp 5' of the translation initiation ATG codon and 34 1 bp of sequences 3' to the translation stop TAG codon.

Plasmid pCGP261 was created as follows. Plasmid pCGN1278 (described in co-pending application U.S. Ser. No. 382, 176, filed Jul. 19, 1989, abandoned, which is hereby incorporated in its entirety by reference) was digested with XbaI and EcoRI. The single-stranded DNA sequences produced were filled in by treatment with the Klenow fragment of DNA polymerase I. The XbaI to EcoRI fragment containing the tmr gene was then ligated into the vector m13 Bluescript minus (Stratagene Inc., La Jolla, Calif.) at the SmaI site, resulting in plasmid pCGP259. All of the region found upstream of the ATG translation initiation codon and some of the tmr gene coding region was eliminated by digesting pCGP259 with BspMI and BstXI. The resulting coding region and 8 bp of the sequence originally found upstream of the first ATG codon was re-introduced into the plasmid and an XbaI site introduced into the plasmid via a synthetic oligonucleotide comprising the following sequence: 5' AATrAGATGCAGGTCCAT-AAGTrHTrCTAGACGCG 3'. The resulting plasmid is pCGP261. An XbaI to KpnI fragment of pCGP261 containing the pZ130 gene 5' and tmr gene coding and 3' region construct was then inserted into a binary cassette such as pCGN1557 and transgenic plants prepared. (See co-pending application U.S. Ser. No. 382,176, abandoned, described above).

EXAMPLE 7

Preparation of pZ130 Promoter Cassette

The pZ130 cassette contains 1.8 kb (pCGN2909) or 5 kb (pCGN2928) of DNA 5' of the translational start site and the 3' region (from the TAA stop codon to a site 1.2 kb downstream) of the pZ130 gene. The pZ130 cassettes were constructed as follows.

Transcriptional Initiation Region

Plasmid DNA isolated from pCGN2901 (see above) was digested to completion with NcoI and then treated with exonuclease isolated from mung bean (Promega, Madison, Wis.) to eliminate single-stranded DNA sequences, including the ATG sequence making up a portion of the NcoI recognition sequence. The sample was then digested to completion with SacI. The resulting 1.8 kb 5' SacI to NcoI fragment was then inserted into pCGN2015 (described above) to create pCGN2904.

In order to eliminate redundant restriction enzyme sites and make subsequent cloning easier, plasmid DNA isolated from pCGN2904 was digested to completion with SalI and EcoRI and the resulting 1.8 kb fragment, containing the pZ130 5' sequences, inserted into pBluescriptII (Stratagene; La Jolla, Calif.) to create pCGN2907.

Transcriptional and Translational Termination Region

Plasmid DNA isolated from pCGN2901 was digested to completion with EcoRI and BamHI. The resulting 0.72 kb EcoRI to BamHI fragment located downstream (3') from the pZ130 coding region was inserted into pCGN2907 creating pCGN2908.

The insertion of the 0.5 kb (approximately) DNA sequence, including the pZ130 gene TAA stop codon and those sequences between the stop codon and the EcoRI site downstream (3') and the addition of unique restriction sites to facilitate insertion of foreign genes, was accomplished as follows.

A polylinker/"primer" comprising the sequence 5'-GTFC-CTGCAGCATGCCCGGGATCGATAATAAT-FAAGTGAGGC-3' was synthesized to create a polylinker with the following sites: PstI-SphI-SmaI-ClaI and to include the pZ130 gene TAA stop codon and the following (3') 13 base pairs of the pZ130 gene 3' region sequence. Another oligonucleotide comprising the sequence 5'-CAAGAATr-CATAATATrATATATAC 3' was synthesized to create a "primer" with an EcoRI restfiction site and 16 base pairs of the pZ130 gene 3'-region immediately adjacent to the EcoRI site located approximately 0.5 kb 3' of the pZ130 gene TAA stop codon.

These synthetic oligonucleotides were used in a polymerase chain reaction (PCR) in which plasmid DNA isolated from pCGN2901 was used as the substrate in a thermal cycler (Perkin-Elmer/Cetus, Norwalk, Conn.) as per the manufacturer's instructions. The resulting 0.5 kb DNA product was digested to completion with PstI and EcoRI and the resulting 0.5 kb DNA fragment inserted into pCGN2908 to create pCGN2909. The complete DNA sequence of the 0.5 kb region from the PstI site to the EcoRI site was determined using the Sanger et at. (1971) dideoxy technique to verify that no mistakes in the sequence had occurred between the oligonucleotide primers during the PCR reaction.

The pZ130 cassette, pCGN2909, thus comprises the 5' pZ130 DNA sequences from the SalI site at position 808 to position 2636 (see FIG. 2), unique PstI, SphI and SmaI sites which can be conveniently used to insert genes, and the 3' pZ130 DNA sequences from the TAA stop codon at position 3173 (FIG. 2) through the BamHI site at position 4380.

EXAMPLE 8

Preparation and Analysis of Test Constructs

A β-glucuronidase (GUS) reporter gene was used to evaluate the expression and tissue specificity of the pZ130-GUS constructions. GLIS is a useful reporter gene in plant systems because it produces a highly stable enzyme, there is little or no background (endogenous) enzyme activity in plant tissues, and the enzyme is easily assayed using fluorescent or spectrophotometric substrates. (See, for example, Jefferson, *Plant Mol. Rep.* (1987) 5:387–405.) Histochemical stains for GUS enzyme activity are also available which can be used to analyze the pattern of enzyme accumulation in transgenic plants. Jefferson (1987), supra.

A pZ130 cassette, pCGN2928, was prepared by inserting the 3.2 KpnI to SalI fragment of pCGN2059 into the KpnI and SalI sites of pCGN2909. pCGN2059 was prepared by inserting the 3.2 SalI to BglII fragment of pCGN2902 into M13mp19. pCGN2928 is thus identical to pCGN2909 except that it includes an additional approximately 3.2 kb of pZ130 DNA sequence upstream of the SalI site located at position 808 of FIG. 2.

Preparation of Test Constructs pCGN2917 and pCGN2918

These constructs contain 1.8 kb of pZ130 5' sequence, the GUS gene coding region and 1.2 kb of pZ130 3' sequence. pCGN2917 and pCGN2918 differ from each other only in the orientation of the pZ130/GUS construction with respect to the other elements of the binary vector plasmid for example, the 35S promoter from CaMV.

The constructs were made by inserting the PstI fragment of pRAJ250 (Jefferson (1987) supra), or any other plasmid construct having the PstI fragment containing the GUS coding region, into the PstI site of pCGN2909. The resulting plasmid, having the GUS gene in the sense orientation with respect to the pZ130 gene promoter region, was named pCGN2914. The pZ130/GUS construction was excised as an XbaI to KpnI fragment and cloned into the binary vectors pCGN1557 and pCGN1558 to make pCGN2917 and pCGN2918, respectively. pCGN1557 and pCGN1558 are described in McBride and Summerfelt, *Plant Mol. Bio.* (1990) 14:269–296.

Preparation of Test Construct pCGN2926

This construct contains 5 kb of pZ130 5' sequence, the GUS gene coding region and 1.2 kb of pZ130 3' sequence. It was made by inserting the 3.2 kb KpnI to SalI fragment of pCGN2059 into the KpnI and SalI sites of pCGN2914. The resulting plasmid was named pCGN2923. The pZ130/GUS/pZ130 construction was then excised from pCGN2923 as an XbaI to KpnI fragment and cloned into the binary vector pCGN1557 resulting in pCGN2926.

Analysis Of GUS Enzyme Activity

β-glucuronidase activity of transformants was measured using 4-methyl-umbelliferyl glucuronide as a substrate, as outlined in Jefferson (1987) supra. GUS enzyme activity was easily detected in the ovaries of the transformed plants and quantitatively was quite high in comparison with the activity background observed in ovaries isolated from nontransformed tomato plants and from leaves of transformed plants. Interestingly, upon comparison of the pCGN2917 and pCGNZ2918 transformants, it was found that proximity to a 35S CaMV enhancer region (pCGN1558) may reduce, or eliminate, ovary-tissue specificity.

EXAMPLE 9

PZ-7 Cotton Transformation

Explant Preparation

Coker 315 seeds were surface disinfected by placing in 50% Clorox® (2.5% sodium hypochlorite solution) for 20 minutes and rinsing 3 times in sterile distilled water. Following surface sterilization, seeds were germinated in 25×150 sterile robes containing 25 mls ½MS salts: ½×B5 vitamins: 1.5% glucose: 0.3% gelrite. Seedlings were germinated in the dark at 28° C. for 7 days. On the seventh day seedlings were placed in the fight at 28°±2° C.

Cocultivation and Plant Regeneration

Single colonies of *A. tumefaciens* strain 2760 containing binary plasmids pCGN2917 and pCGN2926 were transferred to 5 ml of MG/L broth and grown overnight at 30° C. Bacteria cultures were diluted to $1\times10^8$ cells/ml with MG/L just prior to cocultivation. Hypocotyls were excised from eight day old seedlings, cut into 0.5–0.7 cm sections and placed onto tobacco feeder plates (Horsch et al. 1985). Feeder plates were prepared one day before use by plating 1.0 ml tobacco suspension culture onto a petri plate containing Callus Initiation Medium (CIM) without antibiotics (MS salts: B5 vitamins: 3% glucose: 0.1 mg/L 2,4-D: 0.1 mg/L kinetin: 0.3% gelrite, pH adjusted to 5.8 prior to autoclaving). A sterile filter paper disc (Whatman #1) was placed on top of the feeder cells prior to use. After all sections were prepared, each section was dipped into an *A. tumefaciens* culture, blotted on sterile paper towels and returned to the tobacco feeder plates.

Following two days of cocultivation on the feeder plates, hypocotyl sections were placed on fresh Callus Initiation Medium containing 75 mg/L kanamycin and 500 mg/L carbenicillin. Tissue was incubated at 28°±2° C., 30uE 16:8 light:dark period for 4 weeks. At four weeks the entire explant was transferred to fresh callus initiation medium containing antibiotics. After two weeks on the second pass, the callus was removed from the explants and split between Callus Initiation Medium and Regeneration Medium (MS salts: 40 mM $KNO_2$: 10 mM $NH_4Cl$:B5 vitamins:3% glucose:0.3% gelrite:400 mg/L carb:75 mg/L kanamycin).

Embryogenic callus was identified 2–6 months following initiation and was subcultured onto fresh regeneration medium. Embryos were selected for germination, placed in static liquid Embryo Pulsing Medium (Stewart and Hsu medium: 0.01 rag/1 NAA: 0.01 mg/L kinetin: 0.2 mg/L $GA_3$) and incubated overnight at 30° C. The embryos were blotted on paper towels and placed into Magenta boxes containing 40 mls of Stewert and Hsu medium solidified with Gelrite™. Germinating embryos were maintained at 28°±2° C. 50 uE $m^{-2}s^{-1}$ 16:8 photoperiod. Rooted planflets were transferred to soil and established in the greenhouse.

Cotton growth conditions in growth chambers are as follows: 16 hour photoperiod, temperature of approximately 80°–85°, light intensity of approximately 500 µEinsteins. Cotton growth conditions in greenhouses are as follows: 14–16 hour photoperiod with light intensity of at least 400 µEinsteins, day temperature 90°–95° F., night temperature 70°–75° F., relative humidity to approximately 80%.

Plant Analysis

Flowers from greenhouse grown $T_1$ plants were tagged at anthesis in the greenhouse. Squares (cotton flower buds), flowers, bolls etc. were harvested from these plants at various stages of development and assayed for GUS activity. GUS fluorometric and histochemical assays were performed on hand cut sections as described in Jefferson (1987), supra.

At least ten events (transgenic plants) from each construct (pCGN2917 and pCGN2926) were sent to the Growth Chambers/Greenhouse. Approximately 80% (9/11) of the 2917 plants and 100% (12/12) of the 2926 plants expressed GUS at a level detectable by either fluorometric or histochemical assay. Squares from several of pCGN2917 and pCGN2926 transfected plants were assayed for GUS expression using histochemical analysis wherein the cells which are expressing GUS stain blue. Preliminary analysis indicates that all plants expressed GUS in the developing floral parts. Ovules and anthers stained extremely dark. Bracts and locule walls were also blue in some cases. Fibers from 5, 9 and 12 DPA bolls off these plants were also expressing GUS.

Several GUS assays were done on developing bolls at stages from squaring through 53 days post anthesis. GUS activity is very high in squares and flowers. Activity in bolls varies from plant to plant. Activity was present in fiber from two of the 2926 plants at 43 and 53 dpa.

β-glucuronidase is a very stable enzyme; therefore, presence of GUS activity may not be directly correlated in a temporal manner with gene expression, however, the specificity of expression in tissues and/or structures derived from ovary integument was significant. Other tissues not derived from ovary integument, showed no GUS activity above background. Differences in the breakdown of GUS as well as differences in expression may explain the variability of expression patterns.

Comparisons between Cotton and Tomato Expression

An initial MUG assay was done on tissues from tomato and cotton plants transfected with pCGN2917 and pCGN2918. GUS activity was found in tomato roots, stems and leaves as well as meristems, and floral parts. The amount of activity varied from plant to plant. In cotton, activity was highest in floral parts but was detectable in roots and stems of some plants.

T2 tomato plants from 2926 and 2917 are being tagged at anthesis. These plants have been tested for both kan and GUS expression. As the tissue matures it will be assayed and photographed.

EXAMPLE 10

Expression of Transgenic Melanin Synthesis Genes

A binary construct for plant transformation to express genes for melanin synthesis is prepared as follows. The mel operon of *Streptomyces antibioticus* (Bernan et at. (1985) 34:101–110) is subcloned as a BclI fragment into a Bluescript vector. NcoI and BamHI sites are inserted by mutagenesis immediately 5' to (and including) the ATG initiation codon for ORF438. The resulting plasmid is pCGN4229. pCGN4229 is further mutagenized by inserting a PstI site immediately following the ORF438 stop codon and by the addition of NcoI and BamHI sites at the start codon of the tyrA locus, thus, providing the mutagenized mel operon. A PstI site from the plasmid vector is similarly located immediately 3' to the tyrA encoding region.

The pZ130 cassette, pCGN2909, is mutagenized to reinsert the NcoI site including the ATG codon for the initial MET of the pZ130 encoded sequence, and results in pCGN4228. pCGN4228 is mutagenized to delete the BamHI site at the 3' end of the pZ130 transcriptional termination region and to insert an AscI linker fragment in its place, resulting in pCGN4235. pCGN4228 is also mutagenized to deleted the 3' BamHI site and insert an AscI linker 5' to the pZ130 transcriptional initiation region (at XhoI/SalI digested and Klenow treated pCGN4228) resulting in pCGN4241.

The Streptomyces ORF438 region is obtained by digestion of the mutagenized mel operon construct with NcoI and PstI and inserted into Nco/Pst digested pCGN4235. The tyrA region is cloned as an NcoI/PstI fragment from the mutagenized mel operon construct into Nco/Pst digested pCGN4241.

A fragment of the tobacco ribulose bisphosphate carboxylase small subunit gene encoding the transit peptide and 12 amino acids of the mature protein is inserted in reading frame with the ORF438 encoding sequence as an NcoI/BamHI fragment. The fragment is similarly inserted in front of the tyrA encoding sequence. The resulting constructs contain the transit peptide/ORF438 and transit peptide/tryA fusions positioned for expression from the pZ130 5' and 3' regulatory regions.

A binary vector (See FIG. 7) for insertion of the ORF438 and tyrA constructs is prepared from pCGN1578 (McBride et al., supra) by substitution of the pCGN1578 linker region with a linker region containing the following restriction digestion sites: Asp718/Asc/Pac/XbaI/BamHUSwa/Sse/HindIII. (See FIG. 8). This results in pCGN1578PASS. Asc, Pac, Swa and Sse are restriction enzymes that cut at the 8-base recognition sites. The enzymes are available from New England BioLabs: Asc, Pac; Boehringer Manheim-:Swa; and Takara (Japan):Sse.

The ORF438 pZ130 construct is inserted into pCGN1578PASS as an Asp/Asc fragment. The tyrA pZ130 construct is inserted adjacent to the ORF438 pZ130 construct as an Asc/Xba fragment.

As shown by the above results, expression of a gene of interest can be obtained in cells derived from ovary cells, including tomato fruit and cotton fibers.

All publications and patent applications cited in this specification are herein incorporated by reference as if each individual publication or patent application were specifically and individually indicated to be incorporated by reference.

Although the foregoing invention has been described in some detail, by way of illustration and example for purposes of clarity and understanding, it will be readily apparent to those of ordinary skill in the art that certain changes and modifications may be made thereto, without departing from the spirit or scope of the appended claims.

What is claimed is:

1. A DNA construct comprising as operably joined components in the direction of transcription, (a) a transcriptional and translational initiation region from the tomato pZ130 gene functional in a plant ovule integument cell, (b) an open reading frame encoding a melanin synthesis gene product required to synthesize melanin, and (c) a transcriptional termination region.

2. The DNA construct according to claim 1, wherein said open reading frame is ORF438 or from a tyrA gene.

3. The DNA construct according to claim 2, wherein a DNA sequence encoding a transit peptide and first 12 amino acids from a ribulose bisphosphate carboxylase small subunit is placed in front of said open reading frame.

4. A binary vector comprising: one or more DNA constructs according to claim 1, and a selectable marker gene.

5. The binary vector according to claim 4, wherein said vector comprises a first DNA construct encoding a first product and a second DNA construct encoding a second product, and wherein said first product and said second product together are required to synthesize melanin.

6. The binary vector according to claim 5, wherein said first product is a protein encoded by ORF438 and said second product is tyrosinase.

7. A transgenic ovule integument cell, and cells derived from said cell, comprising: one or more DNA constructs according to claim 1.

8. The transgenic ovule integument cell according to claim 7, wherein said cell is a cotton fiber.

9. A transgenic ovule integument cell comprising: a DNA construct according to claim 2.

10. A transgenic plant comprising: cells containing one or more DNA constructs according to claim 1.

11. The transgenic plant according to claim 10, wherein said plant is a cotton plant.

12. Seed from a plant according to claim 10, wherein said seed contains one or more DNA constructs according to claim 1.

13. Plants germinated from the seed according to claim 12.

14. A DNA construct comprising as operably joined components in the direction of transcription,
   (a) a transcriptional and translational initiation region functional in a plant ovule integument cell from the tomato pZ130 gene,
   (b) a DNA sequence encoding a melanin synthesis gene product required to synthesize melanin, wherein said DNA sequence is from a nonplant source,
   (c) and a transcriptional termination region.

15. A transgenic ovule integument cell, and cells derived from said cell, comprising:
   one or more DNA constructs according to claim 1.

16. The transgenic ovule integument cell according to claim 15, wherein said cell is a cotton fiber.

17. A transgenic plant comprising:
   transgenic ovule integument cells according to claim 15.

18. The transgenic plant according to claim 17, wherein said plant is a *Gossypium hirsutum* L. plant.

* * * * *

UNITED STATES PATENT AND TRADEMARK OFFICE
CERTIFICATE OF CORRECTION

PATENT NO.    : 5,530,185
DATED         : June 25, 1996
INVENTOR(S)   : Belinda M. Martineau, David M. Stalker, Ann A. Reilley It is certified that error appears in the above-identified patent and that said Letters Patent is hereby corrected as shown below:

Title page,
Column 1,
Item [63], after "abandoned", insert --; and, also a continuation-in-part of Ser. No. 554,196, filed Jul. 17, 1990, which issued on Jan. 5, 1993, now Pat. No. 5,177,307, which is a continuation-in-part of Ser. No. 382,802, filed Jul. 19, 1989, now abandoned --.

Signed and Sealed this

Twenty-third Day of October, 2001

Attest:

NICHOLAS P. GODICI
Attesting Officer
*Acting Director of the United States Patent and Trademark Office*